United States Patent [19]

Bexten et al.

[11] 4,222,966

[45] Sep. 16, 1980

[54] PROCESS FOR THE MANUFACTURE OF ALDEHYDES

[75] Inventors: Ludger Bexten, Hünxe; Boy Cornils, Dinslaken; Hans-Dieter Hahn; Hans Tummes, both of Oberhausen, all of Fed. Rep. of Germany

[73] Assignee: Ruhrchemie Aktiengesellschaft, Oberhausen, Fed. Rep. of Germany

[21] Appl. No.: 934,668

[22] Filed: Aug. 17, 1978

[30] Foreign Application Priority Data

Aug. 20, 1977 [DE] Fed. Rep. of Germany ....... 2737633

[51] Int. Cl.² .............................................. C07C 45/10
[52] U.S. Cl. ..................................... 568/451; 252/439
[58] Field of Search ..................... 260/604 H, 604 HF; 252/439, 431 R

[56] References Cited

U.S. PATENT DOCUMENTS 3,993,695  11/1976  Tummes et al. .............. 260/604 HF
3,994,978  11/1976  Whitehurst ................... 260/604 HF

FOREIGN PATENT DOCUMENTS 2627354  12/1976  Fed. Rep. of Germany .... 260/604 HF
1326013   8/1973  United Kingdom ............. 260/604 HF Primary Examiner—Werren B. Lone
Attorney, Agent, or Firm—Sprung, Felfe, Horn, Lynch & Kramer

[57] ABSTRACT

An improvement in the process for the continuous manufacture of an aldehyde by reaction of an olefin with carbon monoxide and hydrogen in the presence of a rhodium catalyst at an elevated temperature and pressure followed by distillative separation of the non-converted feedstocks and low boiling components of the reaction mixture, the improvement residing in employing a carbon monoxide/hydrogen mixture containing 2–20 ppm sulfur and recycling residual rhodium compounds, both dissolved and suspended in the distillation residue, to the reaction zone.

18 Claims, No Drawings

PROCESS FOR THE MANUFACTURE OF ALDEHYDES

BACKGROUND OF THE INVENTION

1. Field of the Invention

This invention relates to a process for the manufacture of an aldehyde by reaction of an olefin with carbon monoxide and hydrogen (OXO synthesis) employing a rhodium compound as catalyst. More especially, this invention relates to a process wherein the reaction of carbon monoxide and hydrogen with the olefin is carried out in the presence of sulfur compounds, in particular sulfur compounds present in synthesis gas. This invention is directed particularly to carrying out the OXO synthesis in the presence of sulfur compounds whereby to reduce the amount of fresh rhodium catalyst which would otherwise be required.

2. Discussion of the Prior Art

Rhodium catalysts distinguish themselves in olefin conversions to aldehydes with a unit increase in carbon number, by their great activity and high selectivity. The reaction velocity, which is more than a hundred times greater than with cobalt catalysts, enables the olefin hydroformylation to be conducted using very small quantities of rhodium. While in the cobalt catalyzed hydroformylation 0.1 to 2 percent cobalt are required relative to the olefin feed, for the same olefin conversion, 0.0001 to 0.002 percent rhodium suffices. As a result of the high cost of rhodium compared to cobalt, the catalyst costs are significant in determining the economic efficiency of the process, despite the small catalyst requirement in the commercial OXO rhodium process. For this reason, a number of processes have already been developed which should permit the rhodium catalyst to be recycled thereby reducing the amount of fresh catalyst required.

A rhodium catalyzed process is described in German Offenlegungsschrift 2,406,323 in which olefinic unsaturated compounds are reacted with carbon monoxide and hydrogen in the presence of water.

When the lower boiling components of the reaction product are distilled over, the rhodium remaining in the higher boiling residue can be reintroduced to the synthesis. This process has the disadvantage that, when the lower boiling components of the reaction product are being distilled from the catalyst, large amounts of the rhodium catalyst are deposited on the walls of the distillation column. These amounts are then no longer in the rhodium recycle which must be supplemented by fresh rhodium.

With the other variants of the rhodium-catalyzed OXO process considerable amounts of the initial quantity of rhodium are also lost. It was therefore an object of the invention to develop an OXO process using rhodium catalysts which guarantees a simple and virtually complete recycle of the rhodium catalyst.

SUMMARY OF THE INVENTION

In accordance with this invention the quantity of rhodium lost in a rhodium-catalyzed OXO process is minimized by a process comprising contacting an olefin in the presence of a rhodium compound as catalyst with carbon monoxide and hydrogen at an elevated temperature and pressure, thereafter distillatively separating the non-converted feed components and lower boiling components from the reaction product, the process being improved in that the carbon monoxide/hydrogen mixture employed has a sulfur content of 2 to 20 ppm and dissolved or suspended rhodium compounds present in the distillation residue are recycled as catalyst to the synthesis stage.

Surprisingly, the sulfur- and rhodium-containing residue obtained after distilling over the low boiling components of the reaction product is an effective hydroformylation catalyst which on being continuously recycled to the synthesis exhibited a lower drop in activity compared to a corresponding sulfur-free residue obtained on using sulfur-free synthesis gas.

The catalytic efficacy of the distillation residue was not predictable since it is known that when sulfur compounds react with rhodium carbonyls there is a reduction in the activity of hydroformylation catalysts. Thus until now, the rhodium catalyzed OXO synthesis was operated using feed-stocks which were as sulfur-free as possible. To this end, for example, synthesis gas was subjected to special purification treatment to remove the remaining sulfur present.

The prospect of employing sulfur-containing synthesis gas for the rhodium catalyzed olefin hydroformylation leads to a number of advantages. The new procedure allows cheaper synthesis gas to be employed, as a fine purification for sulfur removal can be dispensed with. Moreover, the maintenance of catalyst concentration and activity necessitates adding a smaller amount of fresh catalyst compared to using sulfur-free synthesis gas.

The surprising effect of sulfur on the rhodium hydroformylation catalysts can be explained by the fact that, in the absence of sulfur, the rhodium carbonyls present in the OXO product can be readily decomposed to insoluble rhodium compounds. Rhodium losses occur via deposition on the walls of the column during the distillation of the OXO raw product to separate the higher boiling components which contain rhodium. Apparently, the rhodium carbonyls present in the OXO raw product, on employing sulfur-containing synthesis gas, do not have these properties as they can be recycled to the synthesis with virtually no loss after distillative separation of the non-converted starting materials and low boiling reaction products. Minor catalyst losses are supplemented in the usual manner by adding fresh catalyst to the catalyst recycle.

The distillative separation of the low boiling components of the reaction products should ensue as quickly as possible at bottom temperatures below 135° C. The most suitable pieces of apparatus are thin-film evaporators, flash and similar distillations which ensure brief heating of the residue which is to be removed but not distilled. Usually, a sulfur content of 5 to 20 ppm, generally as hydrogen sulfide and carbon oxysulfide, is present in the synthesis gas as a consequence of the manufacturing conditions. It is expedient that the hydrogen sulfide content should always be considerably lower than the carbon oxysulfide content. Both sulfur compounds should be present in the ratio $H_2S:COS = 1:2–20$. Higher sulfur contents than 20 ppm should be avoided as they impair the activity of the rhodium catalyst.

The reaction of olefins with synthesis gas containing sulfur ensues at 50° to 200° C. and 5 to 1000 bar. While a solvent may be used, it is not absolutely essential. Carbon monoxide and hydrogen are reacted in molar ratio although it is possible to employ one of the components in excess. Rhodium salts are used as catalyst, during the reaction they are converted into rhodium carbonyl compounds, i.e., substances containing rhodium, carbon monoxide and, if necessary, hydrogen.

The process according to the invention can be employed with olefins possessing between 2 and 18 carbon atoms, e.g., ethylene, propene, butene, isobutene, hexene-1, octene-1, diisobutene, decene-1, dodecene-1, tetradecene-1, hexadecene-1, octadecene-1 or olefin mixtures from the catalytic dehydrogenation of paraffin fractions, from the dehydrochlorination of chlorinated paraffin fractions and from the thermal cracking of paraffin waxes.

In order to more fully illustrate the nature of the invention and the manner of practicing the same, the following examples are presented

EXAMPLES

EXAMPLE 1

The following starting materials are introduced evey hour into the bottom of a 580 l high pressure reactor:
143 kg Diisobutene
8 kg Recycled catalyst
0.1 kg Fresh catalyst (solution of rhodium 2-ethylhexanoate in toluene) with 0.1 g rhodium
70 $Nm^3$ Syntheses gas ($CO:H_2$ ratio = 1:1, sulfur content 1.5 ppm $H_2S$ and 14 ppm COS)

The recycled catalyst consists of the distillation residues from the flash distillation of the OXO product from the same conversion of diisobutene with rhodium (as catalyst). 0.57 g rhodium is present in this recycled catalyst along with the following amounts of organic compounds—2.7 kg $C_9$-aldehyde, 0.5 kg $C_9$-alcohol and 4.8 kg higher boiling substances.

The conversion takes place at 150° C. and 150 bar, the reaction mixture being kept in strong turbulent motion by the synthesis gas feed. The liquid reaction products and the excess gas are removed at the head of the reactor, then after cooling, separated in a high pressure separator into liquid and gaseous products.

A 176 kg liquid product is obtained of the following composition:

| | |
|---|---|
| Isooctane | 2.1 percent |
| Diisobutylene | 25.8 percent |
| $C_9$-aldehyde | 67.4 percent |
| $C_9$-alcohol | 1.5 percent |
| Higher boiling substances | 3.2 percent |

After releasing pressure, the liquid product is separated by means of a flash distillation under reduced pressure (80 torr) and a bottom temperature of 125° C. into a head product and a bottom product containing the catalyst. Every hour, 167.1 kg head product and 8.9 kg bottom product of the following composition are obtained:

| | Head product | Bottom product |
|---|---|---|
| Isooctane | 2.2 percent | — |
| Diisobutylene | 27.2 percent | — |
| $C_9$-aldehyde | 69.3 percent | 30 percent |
| $C_9$-alcohol | 1.3 percent | 5.6 percent |
| Higher boiling substances | — | 64.4 percent |

A conversion of 68.2 percent is attained relative to the diisobutylene feed and, relative to the converted diisobutylene, a theoretical yield of 95.1 percent $C_9$-aldehyde and -alcohol is obtained.

The bottom product with its 0.55 g rhodium content is reintroduced to the reaction after being supplemented with 0.1 g rhodium in the form of a solution of rhodium 2-ethylhexanoate in toluene. After a test run lasting 300 hours using the above standard conditions and introducing a fresh amount of rhodium (0.1 g) every hour, it was found that, on average, the aforementioned yield could be attained. The amount of fresh rhodium introduced was 0.85 ppm, relative to the resulting quantity of $C_9$-alcohol and -aldehyde.

COMPARATIVE EXAMPLE

Using the same apparatus under the same conditions as in Example 1, the sole difference being that a sulfur-free synthesis gas feed is employed, the following substances were introduced every hour:
143 kg Diisobutylene
9 kg Recycled catalyst
0.2 kg Fresh catalyst with 0.18 g rhodium as rhodium 2-ethylhexanoate
70 $Nm^3$ Synthesis gas ($CO:H_2$ ratio = 1:1) sulfur content $H_2S$ < 0.1 ppm, COS 0.1 ppm The recycled catalyst consists of 2.6 kg $C_9$-aldehyde, 0.5 kg $C_9$-alcohol and 5.9 kg higher boiling substances and has a rhodium content of 0.6 g.

177 kg liquid product of the following content were obtained:

| | |
|---|---|
| Isooctane | 2.1 percent |
| Diisobutylene | 26.2 percent |
| $C_9$-aldehyde | 66.4 percent |
| $C_9$-alcohol | 1.7 percent |
| Higher boiling substances | 3.6 percent |

After release of pressure, the liquid product, as described in Example 1, is separated via flash distillation into a head product, containing the reaction product, and bottoms containing the rhodium. Every hour, 167.6 kg head product and 9.4 kg bottom product are obtained with the following composition:

| | Head product | Bottom product |
|---|---|---|
| Isooctane | 2.2 percent | — |
| Diisobutylene | 27.7 percent | — |
| $C_9$-aldehyde | 68.6 percent | 28.7 percent |
| $C_9$-alcohol | 1.5 percent | 5.3 percent |
| Higher boiling substances | — | 66.0 percent |

Relative to the diisobutylene feed, there is 67.6 percent conversion and, relative to the converted diisobutylene, there is a theoretical yield of $C_9$-aldehyde and $C_9$-alcohol of 95.5 percent.

The bottoms, which have a rhodium content of 0.56 g, are supplemented with 0.2 g rhodium in the form of 2-ethylhexanoate and reintroduced to the synthesis.

Compared to the procedure with synthesis gas containing sulfur (Example 1), the average amount of additional rhodium required with the sulfur-free synthesis gas was 1.5 ppm, relative to resulting amount of $C_9$-aldehyde and $C_9$-alcohol, if diisobutylene is reacted to the same extent as with synthesis gas containing sulfur.

There was a general prejudice in the use of sulfur-containing synthesis gas, which has been overcome by the invention.

What is claimed is:

1. In an oxo process for the continuous manufacture of an aldehyde by reaction of an olefin with carbon monoxide and hydrogen at a temperature of 50° to 200° C. under a pressure of 5 to 1,000 bars in the presence of a rhodium catalyst followed by distillative separation of the non-converted feedstocks and low boiling components of the reaction product, the improvement wherein a carbon monoxide/hydrogen mixture containing 2 to 20 parts per million sulfur is employed and residual rhodium catalyst, both dissolved in the distillation residue, are recycled to the reaction zone.

2. A process according to claim 1 wherein the distillation residue is obtained at a distillation temperature below 135° C.

3. A process according to claims 1 or 2 wherein diisobutylene is employed as the olefin feedstock.

4. A process according to claim 1 wherein in addition to dissolved rhodium in the recycle there is a suspended rhodium compound in the recycle.

5. In an oxo process for the continuous manufacture and the continuous separation of an aldehyde from the resultant reaction mixture which process consists essentially of reacting at 50° to 200° C. at a pressure of 5 to 1,000 bars an olefin with carbon monoxide and hydrogen in the presence of a rhodium catalyst followed by distillative separation of the non-converted feedstocks and low boiling components of the reaction product, the improvement wherein a carbon monoxide/hydrogen mixture containing 2 to 20 parts per million sulfur is employed and residual rhodium catalyst, dissolved in the reaction residue, is recycled to the reaction zone.

6. A process according to claim 5 wherein the reaction of the olefin with carbon monoxide and hydrogen is immediately followed by said distillative separation.

7. A process according to claim 5 wherein said distillative separation comprises a flash distillation.

8. A process according to claim 5 wherein both the sulfur and the rhodium compounds are dissolved in the distillation residue and the distillation residue additionally contains suspended rhodium and the dissolved and suspended rhodium compounds together with sulfur are recycled as catalyst to the reaction zone.

9. A process according to claim 1 wherein the olefin is a $C_2$ to $C_{18}$ olefin.

10. A process according to claim 5 wherein the olefin is a $C_2$-$C_{18}$ olefin.

11. A process according to claim 9 wherein said olefin is selected from the group consisting of ethylene, propene, butene, isobutene, hexene-1, octene-1, diisobutene, decene-1, dodecene-1, tetradecene-1, hexadecene-1 and octadecene-1.

12. A process according to claim 10 wherein the olefin is selected from the group consisting of ethylene, propene, butene, isobutene, hexene-1, octene-1, diisobutene, decene-1, dodecene-1, tetradecene-1, hexadecene-1 and octadecene-1.

13. A process according to claim 1 wherein the olefin is a olefin mixture obtained by the catalytic dehydrogenation of a paraffin fraction or an olefin obtained by the dehydrochlorination of a chlorinated paraffin fraction or an olefin obtained by thermal cracking of a paraffin wax.

14. A process according to claim 5 wherein said olefin is a olefin mixture obtained by the catalytic dehydrogenation of a paraffin fraction or an olefin obtained by the dehydrochlorination of a chlorinated paraffin fraction or an olefin obtained by thermal cracking of a paraffin wax.

15. A process according to claim 9 wherein the sulfur is supplied in the form of hydrogen sulfide.

16. A process according to claim 9 wherein the sulfur is employed in the form of carbon oxysulfide.

17. A process according to claim 10 wherein the sulfur is supplied in the form of hydrogen sulfide.

18. A process according to claim 10 wherein the sulfur is supplied in the form of carbon oxysulfide.

* * * * *